US009204996B2

(12) United States Patent
Till et al.

(10) Patent No.: US 9,204,996 B2
(45) Date of Patent: *Dec. 8, 2015

(54) PRESBYOPIA TREATMENT BY LENS ALTERATION

(71) Applicant: Encore Health, LLC, Roanoke, VA (US)

(72) Inventors: Jonathan S. Till, Roanoke, VA (US); Ronald D. Blum, Roanoke, VA (US)

(73) Assignee: Encore Health, LLC, Roanoke, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/275,511

(22) Filed: May 12, 2014

(65) Prior Publication Data

US 2014/0336562 A1 Nov. 13, 2014

Related U.S. Application Data

(60) Division of application No. 13/028,766, filed on Feb. 16, 2011, now Pat. No. 8,747,829, which is a division of application No. 11/010,436, filed on Dec. 14, 2004, now Pat. No. 7,935,332, which is a continuation of application No. 10/050,879, filed on Jan. 18, 2002, now Pat. No. 6,923,955, which is a continuation-in-part of application No. 09/930,287, filed on Aug. 16, 2001, now abandoned.

(60) Provisional application No. 60/225,659, filed on Aug. 16, 2000, provisional application No. 60/262,423, filed on Jan. 19, 2001.

(51) Int. Cl.
| | |
|---|---|
| *A61K 31/74* | (2006.01) |
| *A61F 9/013* | (2006.01) |
| *A61K 9/00* | (2006.01) |
| *A61F 9/007* | (2006.01) |
| *A61K 38/06* | (2006.01) |
| *A61K 38/45* | (2006.01) |
| *A61K 41/00* | (2006.01) |
| *A61F 9/00* | (2006.01) |

(52) U.S. Cl.
CPC .............. *A61F 9/013* (2013.01); *A61F 9/007* (2013.01); *A61F 9/0017* (2013.01); *A61F 9/0079* (2013.01); *A61K 9/0048* (2013.01); *A61K 38/063* (2013.01); *A61K 38/45* (2013.01); *A61K 41/00* (2013.01); *A61K 41/0023* (2013.01); *A61K 41/0042* (2013.01)

(58) Field of Classification Search
CPC .................................................. A61K 9/0048
See application file for complete search history.

(56) References Cited

U.S. PATENT DOCUMENTS

| | | | |
|---|---|---|---|
| 3,238,224 A | | 3/1966 | Ohara et al. |
| 3,855,240 A | | 12/1974 | Mueller |
| 4,210,667 A | | 7/1980 | Sarges et al. |
| 4,755,528 A | | 7/1988 | DuPriest et al. |
| 5,395,356 A | | 3/1995 | King et al. |
| 5,459,133 A | | 10/1995 | Neufeld |
| 5,465,737 A | | 11/1995 | Schachar |
| 5,466,680 A | | 11/1995 | Rudy |
| 5,476,515 A | | 12/1995 | Kelman et al. |
| 5,488,050 A | | 1/1996 | Neufeld |
| 5,503,165 A | | 4/1996 | Schachar |
| 5,527,774 A | | 6/1996 | Giard |
| 5,529,076 A | | 6/1996 | Schachar |
| 5,624,955 A | | 4/1997 | Nagasawa et al. |
| 5,665,770 A | | 9/1997 | Treao et al. |
| 5,686,450 A | | 11/1997 | Hellberg et al. |
| 5,688,828 A | | 11/1997 | Hellberg et al. |
| 5,691,379 A | | 11/1997 | Ulrich et al. |
| 5,722,952 A | | 3/1998 | Schachar |
| 5,817,630 A | * | 10/1998 | Hofmann et al. ............ 514/20.8 |
| 5,843,184 A | | 12/1998 | Cionni |
| 5,869,468 A | | 2/1999 | Freeman |
| 5,874,455 A | | 2/1999 | Terao et al. |
| 5,888,243 A | | 3/1999 | Silverstrini |
| 6,007,510 A | | 12/1999 | Nigam |
| 6,013,462 A | | 1/2000 | Kauvar et al. |
| 6,030,950 A | | 2/2000 | Ohlenschlager |

(Continued)

FOREIGN PATENT DOCUMENTS

| | | |
|---|---|---|
| EP | 0 369 880 | 5/1990 |
| WO | WO 93/25166 | 12/1993 |

(Continued)

OTHER PUBLICATIONS

Al-Ghoul, K. J., R. K. Nordgren, A. J. Kuszak, C. D. Freel, M. J. Costello, and J. R. Kuszak. 2001. Structural evidence of human nuclear fiber compaction as a function of ageing and cataractogenesis. Experimental eye research 72: 199-214.

Applegate, M. A., K. M. Humphries, and L. I. Szweda. Jan. 2007. Reversible Inhibition of alpha-Ketoglutarate Dehydrogenase by Hydrogen Peroxide: Glutathionylation and Protection of Lipoic Acid. Biochemistry. 47(1): 473-478.

Argirova, M., M. Kleine-Reidick, and W. Breipohl. 2004. Redox status of the eye lens: a regional study. Cell biochemistry and biophysics 41: 381-390.

(Continued)

*Primary Examiner* — Carlos Azpuru
(74) *Attorney, Agent, or Firm* — Sterne, Kessler, Goldstein & Fox P.L.L.C.

(57) ABSTRACT

This invention effects a change in the accommodation of the human lens affected by presbyopia through the use of various reducing agents that change accommodative abilities of the human lens, and/or by applying energy to affect a change in the accommodative abilities of the human lens. This invention both prevents the onset of presbyopia as well as treats it. By breaking and/or preventing the formation of bonds that adhere lens fibers together causing hardening of the lens, the present invention increases the elasticity and distensibility of the lens and/or lens capsule.

14 Claims, No Drawings

(56) References Cited

U.S. PATENT DOCUMENTS

| | | | |
|---|---|---|---|
| 6,063,116 | A | 5/2000 | Kelleher |
| 6,214,044 | B1 | 4/2001 | Silverstrini |
| 6,288,106 | B1 | 9/2001 | Pearson et al. |
| 6,313,164 | B1 | 11/2001 | Fujita et al. |
| 6,339,102 | B1 | 1/2002 | Meyerhoff et al. |
| 6,387,945 | B2 | 5/2002 | Packer et al. |
| 6,472,541 | B2 | 10/2002 | Tsien et al. |
| 6,664,287 | B2 | 12/2003 | Avery et al. |
| 6,703,039 | B2 | 3/2004 | Xia et al. |
| 6,743,779 | B1 | 6/2004 | Unger et al. |
| 6,923,955 | B2 | 8/2005 | Till et al. |
| 7,164,943 | B2 | 1/2007 | Roy |
| 7,914,815 | B2 | 3/2011 | Till et al. |
| 7,935,332 | B2 | 5/2011 | Till |
| 8,147,816 | B2 | 4/2012 | Till et al. |
| 8,410,162 | B2 | 4/2013 | Garner et al. |
| 8,647,612 | B2 | 2/2014 | Garner et al. |
| 8,697,109 | B2 | 4/2014 | Garner et al. |
| 8,747,829 | B2 | 6/2014 | Till et al. |
| 2002/0025311 | A1 | 2/2002 | Till |
| 2002/0035243 | A1 | 3/2002 | Imfeld et al. |
| 2003/0187058 | A1 | 10/2003 | Hasselwander et al. |
| 2003/0228299 | A1 | 12/2003 | Droy-Lefaix et al. |
| 2004/0044227 | A1 | 3/2004 | Klatt et al. |
| 2004/0092586 | A1 | 5/2004 | Ogata et al. |
| 2005/0101677 | A1 | 5/2005 | Till |
| 2005/0112113 | A1 | 5/2005 | Till et al. |
| 2005/0130881 | A1 | 6/2005 | Shashoura et al. |
| 2005/0137124 | A1 | 6/2005 | Castillejos |
| 2005/0171212 | A1 | 8/2005 | Gierhart et al. |
| 2005/0287201 | A1 | 12/2005 | Till et al. |
| 2006/0177430 | A1 | 8/2006 | Bhushan |
| 2006/0188492 | A1 | 8/2006 | Richardson et al. |
| 2007/0055070 | A1 | 3/2007 | Lawrence |
| 2007/0207116 | A1 | 9/2007 | Brown |
| 2007/0293562 | A1 | 12/2007 | Mylari et al. |
| 2008/0038316 | A1 | 2/2008 | Wong et al. |
| 2008/0139990 | A1 | 6/2008 | Till et al. |
| 2008/0213239 | A1 | 9/2008 | Morris |
| 2009/0082281 | A1 | 3/2009 | Shashoua |
| 2009/0093541 | A1 | 4/2009 | Ogata |
| 2009/0192212 | A1 | 7/2009 | Garner et al. |
| 2009/0227677 | A1 | 9/2009 | Garner et al. |
| 2010/0098653 | A1 | 4/2010 | Yu et al. |
| 2010/0317608 | A1 | 12/2010 | Garner et al. |
| 2011/0135622 | A1 | 6/2011 | Till et al. |
| 2014/0121266 | A1 | 5/2014 | Garner et al. |

FOREIGN PATENT DOCUMENTS

| | | |
|---|---|---|
| WO | WO 93/25199 | 12/1993 |
| WO | WO 94/01773 | 1/1994 |
| WO | WO 02/13863 | 2/2002 |
| WO | WO 02/056804 | 7/2002 |
| WO | WO 03/084532 | 10/2003 |
| WO | WO 2004/028536 | 4/2004 |
| WO | WO 2005/084635 | 9/2005 |
| WO | WO 2006/047080 | 5/2006 |
| WO | WO 2007/011874 | 1/2007 |
| WO | WO 2008/120070 | 10/2008 |
| WO | WO 2010/054135 | 5/2010 |
| WO | WO 2010/147962 | 12/2010 |

OTHER PUBLICATIONS

Ariga T, et al. 2000. Antithrombotic and antineoplastic effects of phyto-organosulfur compounds. Biofactors. 13(1-4):251-5.

Arora A, et al. 2004. Reversal of P-glycoprotein-mediated multidrug resistance by diallyl sulfide in K562 leukemic cells and in mouse liver. Carcinogenesis. 25(6):941-9. Epub Jan. 16, 2004.

Asmellash S, et al. 2005. Modulating the endoplasmic reticulum stress response with trans-4,5-dihydroxy-1,2-dithiane prevents chemically induced renal injury in vivo. Toxicol Sci. 88(2):576-84. Epub Sep. 8, 2005.

Baghieri, S., and M. H. Garner. 1992. Na,K-ATPase and phospholipid degradation in bovine and human lenses. Current eye research 11: 459-467.

Belloir C, et al. 2006. Protective effects of garlic sulfur compounds against DNA damage induced by direct- and indirect-acting genotoxic agents in HepG2 cells. Food Chem Toxicol. 44(6):827-34.

Bilska, A., and L. Wlodek. 2005, Lipoic acid—the drug of the future? Pharmacol Rep 57: 570-577.

Bilska, A., M. Dubiel, M. Sokolowska-Jezewicz, E. Lorenc-Koci, and L. Wlodek. Jun. 2007. Alpha-lipoic acid differently affects the reserpine-induced oxidative stress in the striatum and prefrontal cortex of rat brain. Neuroscience 146: 1758-1771.

Bitar, M. S., S. Wahid, C. W. Pilcher, E. Al-Saleh, and F. Al-Mulla. 2004. Alpha-lipoic acid mitigates insulin resistance in Goto-Kakizaki rats. Hormone and metabolic research. Hormon- und Stoffwechselforschung 36: 542-549.

Blanco, R. A., T. R. Ziegler, B. A. Carlson, P. Y. Cheng, Y. Park, G. A. Cotsonis, C. J. Accardi, and D. P. Jones. Oct. 2007. Diurnal variation in glutathione and cysteine redox states in human plasma. The American journal of clinical nutrition 86: 1016-1023.

Blankenship, T. N., J. F. Hess, and P. G. FitzGerald. 2001. Development- and differentiation-dependent reorganization of intermediate filaments in fiber cells. Investigative ophthalmology & visual science 42: 735-742.

Bonomi, L et al. 1990. Evaluation of the 701 interzeag lens opacity meter. Graefe's Arch Clin Exp Ophthalmol 228(5):447-9.

Borja, D et al. Jun. 2008. Optical Power of the Isolated Human Crystalline Lens. Invest Ophthalmol Vis Sci 49(6):2541-8.

Bron, A.J., et al. "The Ageing Lens" Ophthalmologica (2000) 214(1):86-104.

Brunkener, M., and S. D. Georgatos. 1992. Membrane-binding properties of filensin, a cytoskeletal protein of the lens fiber cells. Journal of cell science 103 ( Pt 3): 709-718.

Cenedella, R. J. 1998. Prenylation of proteins by the intact lens. Investigative ophthalmology & visual science 39: 1276-1280.

Croft, M. A., A. Glasser, G. Heatley, J. McDonald, T. Ebbert, N. V. Nadkarni, and P. L. Kaufman. 2006. The zonula, lens, and circumlental space in the normal iridectomized rhesus monkey eye. Investigative ophthalmology & visual science 47: 1087-1095.

Croft, M. A., and P. L. Kaufman. 2006. Accommodation and presbyopia: the ciliary neuromuscular view. Ophthalmology clinics of North America 19: 13-24, v.

Dubbelman, M., G. L. Van der Heijde, H. A. Weeber, and G. F. Vrensen. 2003. Changes in the internal structure of the human crystalline lens with age and accommodation. Vision research 43: 2363-2375.

Eason, R. C., H. E. Archer, S. Akhtar, and C. J. Bailey. 2002. Lipoic acid increases glucose uptake by skeletal muscles of obese-diabetic ob/ob mice. Diabetes Obes Metab 4: 29-35.

Egan, D., P. James, D. Cooke, and R. O'Kennedy. 1997. Studies on the cytostatic and cytotoxic effects and mode of action of 8-nitro-7-hydroxycoumarin. Cancer letters 118: 201-211.

Finn, G., B. Creaven, and D. Egan. 2003. Modulation of mitogen-activated protein kinases by 6-nitro-7-hydroxycoumarin mediates apoptosis in renal carcinoma cells. European journal of pharmacology 481: 159-167.

Finn, G. J., B. S. Creaven, and D. A. Egan. 2004. A study of the role of cell cycle events mediating the action of coumarin derivatives in human malignant melanoma cells. Cancer letters 214: 43-54.

Flammer J, Bebie H. 1987. Lens Opacity Meter: a new instrument to quantify lens opacity. Ophthalmologica 195(2):69-72.

Furuta, T., S. S. Wang, J. L. Dantzker, T. M. Dore, W. J. Bybee, E. M. Callaway, W. Denk, and R. Y. Tsien. 1999. Brominated 7-hydroxycoumarin-4-ylmethyls: photolabile protecting groups with biologically useful cross-sections for two photon photolysis. Proceedings of the National Academy of Sciences of the United States of America 96: 1193-1200.

Gail MH & You WC. 2006. A factorial trial including garlic supplements assesses effect in reducing precancerous gastric lesions. J Nutr. 136(3 Suppl):813S-815S.

Garner, M. H., and J. Horwitz. 1994. Catalytic subunit isoforms of mammalian lens Na,K-ATPase. Current eye research 13: 65-77.

(56) References Cited

OTHER PUBLICATIONS

Garner, M. H., and Y. Kong. 1999. Lens epithelium and fiber Na,K-ATPases: distribution and localization by immunocytochemistry. Investigative ophthalmology & visual science 40: 2291-2298.

Garner, M. H., and J. R. Kuszak. 1993. Cations, oxidants, light as causative agents in senile cataracts. Puerto Rico health sciences journal 12: 115-122.

Garner, M. H., and A. Spector. 1980. Selective oxidation of cysteine and methionine in normal and senile cataractous lenses. Proceedings of the National Academy of Sciences of the United States of America 77: 1274-1277.

Garner, M. H. 1994. Na,K-ATPases of the lens epithelium and fiber cell: formation of catalytic cycle intermediates and Na+: K+ exchange. Experimental eye research 58: 705-718.

Gilmore WJ & Kirby GM. 2004. Endoplasmic reticulum stress due to altered cellular redox status positively regulates murine hepatic CYP2A5 expression. J Pharmacol Exp Ther. 308(2):600-8. Epub Nov. 10, 2003.

Glasser, A., and M. C. Campbell. 1999. Biometric, optical and physical changes in the isolated human crystalline lens with age in relation to presbyopia. Vision research 39: 1991-2015.

Goulielmos, G., F. Gounari, S. Remington, S. Muller, M. Haner, U. Aebi, and S. D. Georgatos. 1996. Filensin and phakinin form a novel type of beaded intermediate filaments and coassemble de novo in cultured cells. The Journal of cell biology 132: 643-655.

Goulielmos, G., S. Remington, F. Schwesinger, S. D. Georgatos, and F. Gounari, 1996. Contributions of the structural domains of filensin in polymer formation and filament distribution. Journal of cell science 109 ( Pt 2): 447-456.

Green DR & Reed JC. 1998. Mitochondria and apoptosis. Science 281(5381):1309-12.

Gruzman, A., A. Hidmi, J. Katzhendler, A. Haj-Yehie, and S. Sasson. 2004. Synthesis and characterization of new and potent alpha-lipoic acid derivatives. Bioorganic & medicinal chemistry 12: 1183-1190.

Guest, P. C., H. A. Skynner, K. Salim, F. D. Tattersall, M. R. Knowles, and J. R. Atack. 2006. Detection of gender differences in rat lens proteins using 2-D-DIGE. Proteomics 6: 667-676.

Gurney, AM. 1994. Flash photolysis of caged compounds in Microelectrode Techniques, ed Ogden D, pp. 389-406.

Halhal M, et al. 2004, Iontophoresis: from the lab to the bed side. Exp Eye Res 78(3):751-57.

Halleck MM, et al. 1997. Reduction of trans-4,5-dihydroxy-1,2-dithiane by cellular oxidoreductases activates gadd153/chop and grp78 transcription and induces cellular tolerance in kidney epithelial cells. J Biol Chem. 272(35):21760-6.

Hardie, R.C. 1995. Photolysis of Caged Ca2+ Facilitates and inactivates but Does Not Directly Excite Light-Sensitive Channels in Drosophila Photoreceptors. The Journal of Neuroscience 15(1):899-902.

Heidemann, S. R., S. Kaech, R. E. Buxbaum, and A. Matus. 1999. Direct observations of the mechanical behaviors of the cytoskeleton in living fibroblasts. The Journal of cell biology 145: 109-122.

Hermans, E., M. Dubbelman, R. van der Heijde, and R. Heethaar. Jul. 2007. The shape of the human lens nucleus with accommodation. Journal of vision 7: 16.1-10.

Hoenders, H.J., et al. "Lens proteins and aging" J Gerontol (May 1983) 38(3):278-86.

Hofinarin, M., P. Mainka, H. Tritschler, J. Fuchs, and G. Zimmer. 1995. Decrease of red cell membrane fluidity and -SH groups due to hyperglycemic conditions is counteracted by alpha-lipoic acid. Archives of biochemistry and biophysics 324: 85-92.

Hung CC, et al. 2003. Protection of renal epithelial cells against oxidative injury by endoplasmic reticulum stress preconditioning is mediated by ERK1/2 activation. J Biol Chem. 278(31):29317-26. Epub May 8, 2003.

Ivanov, D., G. Dvoriantchikova, A. Pestova, L. Nathanson, and V. I. Shestopalov. 2005. Microarray analysis of fiber cell maturation in the lens. FEBS letters 579: 1213-1219.

Janoria, K. G., S. Hariharan, D. Paturi, D. Pal, and A. K. Mitra. 2006. Biotin uptake by rabbit corneal epithelial cells: role of sodium-dependent multivitamin transporter (SMVT). Current eye research 31: 797-809.

Jimenez-Orozco, F. A., J. S. Lopez-Gonzalez, A. Nieto-Rodriguez, M. A. Velasco-Velazquez, J. A. Molina-Guarneros, N. Mendoza-Patino, M. J. Garcia-Mondragon, P. Elizalde-Galvan, F. Leon-Cedeno, and J. J. Mandoki. 2001. Decrease of cyclin D1 in the human lung adenocarcinoma cell line A-427 by 7-hydroxycoumarin. Lung cancer (Amsterdam, Netherlands) 34: 185-194.

Johansson, M., and M. Lundberg. Dec. 2007. Glutathionylation of beta-actin via a cysteinyl sulfenic acid intermediary. BMC Biochem 8: 26.

Jones, D. P., Y. M. Go, C. L. Anderson, T. R. Ziegler, J. M. Kinkade, Jr., and W. G. Kirlin. 2004. Cysteine/cystine couple is a newly recognized node in the circuitry for biologic redox signaling and control. Faseb J 18: 1246-1248.

Jung MY, et al. 2001. Chemopreventive allylthiopyridazine derivatives induce apoptosis in SK-Hep-1 hepatocarcinoma cells through a caspase-3-dependent mechanism. Eur J Cancer. 37(16):2104-10.

Jürgen, W. Mar. 2007. Synthesis and investigations of (6-hydroxy-3-oxo-3H-xanthen-9-yl)methyl derivatives. A new photoremovable protecting group. Inaugural Dissertation at Universität Basel.

Kahn, J., P. Preis, F. Waldman, and A. Tseng, Jr. 1994. Coumarin modulates the cell-cycle progression of an MTV-EJras cell line. Journal of cancer research and clinical oncology 120 Suppl: S19-22.

Kao, J.P.Y. 2006. Caged Molecules: Principles and Practical Considerations. Current Protocols in Neuroscience. 6.20.1-6.20.21.

Kibbelaar, M. A., F. C. Ramaekers, P. J. Ringens, A. M. Selten-Versteegen, L. G. Poels. P. H. Jap, A. L. van Rossum, T. E. Feltkamp, and H. Bloemendal. 1980. Is actin in eye lens a possible factor in visual accomodation? Nature 285: 506-508.

Kim DH, et al. 2005. Aqueous penetration and biological activity of moxifloxacin 0.5% ophthalmic solution and gatifloxacin 0.3% solution in cataract surgery patients. Ophthalmology 112(11):1992-6. Epub Sep. 23, 2005.

Konrad, D., R. Somwar, G. Sweeney, K. Yaworsky, M. Hayashi, T. Ramlal, and A. Klip, 2001. The antihyperglycemic drug alpha-lipoic acid stimulates glucose uptake via both GLUT4 translocation and GLUT4 activation: potential role of p38 mitogen-activated protein kinase in GLUT4 activation. Diabetes 50: 1464-1471.

Krueger, R.R., et al. "Experimental increase in accommodative potential after neodymium: yttrium—aluminum-garnet laser photodisruption of paired cadaver lenses" Ophthalmology (2001) 108(11):2122-29.

Krumdieck, C.L., et al. "Mechanism of Homocysteine Toxicity on Connective Tissues: Implications for the Morbidity of Aging" J. Nutr. (2000) 130:365S-68S.

Kumar RV, et al. 1991. The nature of inhibition of 3-hydroxy-3-methylglutaryl CoA reductase by garlic-derived diallyl disulfide. Biochim Biophys Acta. 1078(2):219-25.

Kuszak, J. R., A. R. Khan, and R. J. Cenedella. 1988. An ultrastructural analysis of plasma membrane in the U18666A cataract. Investigative ophthalmology & visual science 29: 261-267.

Lacy, A., and R. O'Kennedy. 2004. Studies on coumarins and coumarin-related compounds to determine their therapeutic role in the treatment of cancer. Current pharmaceutical design 10: 3797-3811.

Larsson, H. P., A. V. Tzingounis, H. P. Koch, and M. P. Kavanaugh. 2004. Fluorometric measurements of conformational changes in glutamate transporters. Proceedings of the National Academy of Sciences of the United States of America 101: 3951-3956.

Lee V & Bundgaard H. 1992. Improved Ocular Drug Delivery with Prodrugs. In: Sloan K. ed. Produgs: Topical and Ocular Drug Delivery, vol. 53, p. 233.

Lesiński L. & Duschmalé J. 2006. Flash Photolysis in Praktikum "Physikalische Chemie" pp. 1-8.

Li, L., J. Lim, M. D. Jacobs, J. Kistler, and P. J. Donaldson, Mar. 2007. Regional differences in cystine accumulation point to a sutural delivery pathway to the lens core, Investigative ophthalmology & visual science 48: 1253-1260.

Lim, J., Y. C. Lam, J. Kistler, and P. J. Donaldson. 2005. Molecular characterization of the cystine/glutamate exchanger and the excita-

(56) References Cited

OTHER PUBLICATIONS tory amino acid transporters in the rat lens. Investigative ophthalmology & visual science 46: 2869-2877.

Lim, J., L. Li, M. D. Jacobs, J. Kistler, and P. J. Donaldson. Nov. 2007. Mapping of glutathione and its precursor amino acids reveals a role for GLYT2 in glycine uptake in the lens core. Investigative ophthalmology & visual science 48: 5142-5151.

Lindsey Rose, K. M., R. G. Gourdie, A. R. Prescott, R. A. Quinlan, R. K. Crouch, and K. L. Schey. 2006. The C terminus of lens aquaporin 0 interacts with the cytoskeletal proteins filensin and CP49. Investigative ophthalmology & visual science 47: 1562-1570.

Liu H, et al. 1997. Endoplasmic reticulum chaperones GRP78 and calreticulin prevent oxidative stress, Ca2+ disturbances, and cell death in renal epithelial cells. J Biol Chem. 272(35):21751-9.

Liu, J., E. Head, A. M. Gharib. W. Yuan, R. T. Ingersoll, T. M. Hagen, C. W. Cotman, and B. N. Ames, 2002. Memory loss in old rats is associated with brain mitochondrial decay and RNA/DNA oxidation: partial reversal by feeding acetyl-L-carnitine and/or R-alpha-lipoic acid. Proceedings of the National Academy of Sciences of the United States of America 99: 2356-2361.

Lopez-Gonzalez, J. S., H. Prado-Garcia, D. Aguilar-Cazares, J. A. Molina-Guarneros, J. Morales-Fuentes, and J. J. Mandoki. 2004. Apoptosis and cell cycle disturbances induced by coumarin and 7-hydroxycotimarin on human lung carcinoma cell lines. Lung cancer (Amsterdam, Netherlands) 43: 275-283.

Luo, S., V. S. Kansara, X. Zhu, N. K. Mandava, D. Pal, and A. K. Mitra. 2006. Functional characterization of sodium-dependent multivitamin transporter in MDCK-MDR1 cells and its utilization as a target for drug delivery. Mol Pharm 3: 329-339.

Maitra, I., E. Serbinova, H. J. Tritschler, and L. Packer. 1996. Stereospecific effects of R-lipoic acid on buthionine sulfoximine-induced cataract formation in newborn rats. Biochemical arid biophysical research communications 221: 422-429.

Maitra, I., E. Serbinova, H. Trischler, and L. Packer. 1995. Alpha-lipoic acid prevents buthionine sulfoximine-induced cataract formation in newborn rats. Free radical biology & medicine 18: 823-829.

Manns, F., J. M. Parel, D. Denham, C. Billotte, N. Ziebarth, D. Borja, V. Fernandez, M. Aly, E. Arrieta, A. Ho, and B. Holden. Jul. 2007. Optomechanical response of human and monkey lenses in a lens stretcher. Investigative ophthalmology & visual science 48: 3260-3268.

Merdes, A., M. Brunkener, H. Horstmann, and S. D. Georgatos. 1991. Filensin: a new vimentin-binding, polymerization-competent, and membrane-associated protein of the lens fiber cell. The Journal of cell biology 115: 397-410.

Merdes, A., F. Gounari, and S. D. Georgatos. 1993. The 47-kD lens-specific protein phakinin is a tailless intermediate filament protein and an assembly partner of filensin. The Journal of cell biology 123: 1507-1516.

Moffat, B.A., et al. "Age-related Changes in the Kinetics of Water Transport in Normal Human Lenses" Exp. Eye Res. (1999) 69(6):663-69.

Moini, H., O. Tirosh, Y. C. Park, K. J. Cho, and L. Packer. 2002. R-alpha-lipoic acid action on cell redox status, the insulin receptor, and glucose uptake in 3T3-L1 adipocytes. Archives of biochemistry and biophysics 397: 384-391.

Muchowski, P. J., M. M. Valdez, and J. I. Clark. 1999. AlphaB-crystallin selectively targets intermediate filament proteins during thermal stress. Investigative ophthalmology & visual science 40: 951-958.

Musk SR, et al. 1997. Cytotoxicity and genotoxicity of diallyl sulfide and diallyl disulfide towards Chinese hamster ovary cells. Food Chem Toxicol. 35(3-4):379-85.

Newell. 1996. Ophthalmology: Principles and Concepts St. Louis: Mosby-Year Book St. Louis, p. 83.

Obrosova I, et al. 1998. Diabetes-induced changes in lens antioxidant status, glucose utilization and energy metabolism: effect of DL-alpha-lipoic acid. Diabetologia 41(12):1442-50.

Ong, M. D., D. M. Payne, and M. H. Garner. 2003. Differential protein expression in lens epithelial whole-mounts and lens epithelial cell cultures. Experimental eye research 77: 35-49.

Pau, H., and J. Kranz. 1991. The increasing sclerosis of the human lens with age and its relevance to accommodation and presbyopia. Graefe's archive for clinical and experimental ophthalmology=Albrecht von Graefes Archiv fur klinische und experimentelle Ophthalmologie 229: 294-296.

Petit PX, et al. 1995. Alterations in mitochondrial structure and function are early events of dexamethasone-induced thymocyte apoptosis. J Cell Biol. 130(1):157-67.

Phelps-Brown, N. A., et al. "Nutritional supplements and the eye" Eye (1998) 12:127-33.

Pierscionek, B. K. 1995. Age-related response of human lenses to stretching forces. Experimental eye research 60: 325-332.

Reddy, N. S., K. Gumireddy, M. R. Mallireddigari, S. C. Cosenza, P. Venkatapuram, S. C. Bell, E. P. Reddy, and M. V. Reddy. 2005. Novel coumarin-3-(N-aryl)carboxamides arrest breast cancer cell growth by inhibiting ErbB-2 and ERK1. Bioorganic & medicinal chemistry 13: 3141-3147.

Salvioli S, et al. 1997. JC-1, but not DiOC6(3) or rhodamine 123, is a reliable fluorescent probe to assess delta psi changes in intact cells: implications for studies on mitochondrial functionality during apoptosis. FEBS Lett. 411(1):77-82.

Sandilands, A., A. R. Prescott, A. M. Hutcheson, R. A. Quinlan, J. T. Casselman, and P. G. FitzGerald. 1995. Filensin is proteolytically processed during lens fiber cell differentiation by multiple independent pathways. European journal of cell biology 67: 238-253.

Sarraf D & Lee DA. 1994. The Role of Iontophoresis in Ocular Drug Delivery. J Ocul Pharmacol 10(1):69-81.

Sato, H., M, Tamba, K. Kuriyama-Matsumura, S. Okuno, and S. Bannai. 2000. Molecular cloning and expression of human xCT, the light chain of amino acid transport system xc. Antioxid Redox Signal 2: 665-671.

Sato, H., M. Tamba, T. Ishii, and S. Bannai. 1999. Cloning and expression of a plasma membrane cystine/glutamate exchange transporter composed of two distinct proteins. The Journal of biological chemistry 274: 11455-11458.

Sato, H., A. Shiiya, M. Kimata, K. Maebara, M. Tamba, Y. Sakakura, N. Makino, F. Sugiyama, K. Yagami, T. Moriguchi, S. Takahashi, and S. Bannai. 2005. Redox imbalance in cystine/glutamate transporter-deficient mice. The Journal of biological chemistry 280: 37423-37429.

Schonheit, K., L. Gille, and H. Nohl. 1995. Effect of alpha-lipoic acid and dihydrolipoic acid on ischemia/reperfusion injury of the heart and heart mitochondria. Biochimica et biophysica acta 1271: 335-342.

Senda, N. 2006. Synthesis and Photochemical Properties of a New Water-Soluble Coumarin, Designed as a Chromophore for Highly Water-Soluble and Photolabile Protecting Group. Bull. Chem. Soc. Jpn. vol. 79, No. 11, 1753-1757.

Shembekar, V. R., Y. Chen, B. K. Carpenter, and G. P. Hess. 2005. A protecting group for carboxylic acids that can be photolyzed by visible light. Biochemistry 44: 7107-7114.

Spector, A., et al. "Thioredoxin fragment 31-36 is reduced by dihydrolipoamide and reduces oxidized protein" Biochem Biophys Res Common (Jan. 1988) 150(1):156-62.

Strenk, S. A., L. M. Strenk, J. L. Semmlow, and J. K. DeMarco. 2004. Magnetic resonance imaging study of the effects of age and accommodation on the human lens cross-sectional area. Investigative ophthalmology & visual science 45: 539-545.

Sundaram SG & Milner JA. 1996. Diallyl disulfide suppresses the growth of human colon tumor cell xenografts in athymic nude mice. J Nutr. 126(5):1355-61.

Sweeney, M. H., and R. J. Truscott, 1998. An impediment to glutathione diffusion in older normal human lenses: a possible precondition for nuclear cataract. Experimental eye research 67: 587-595.

Tamm, E., E. Lutjen-Drecoll, W. Jungkunz, and J. W. Rohen. 1991. Posterior attachment of ciliary muscle in young, accommodating old, presbyopic monkeys. Investigative ophthalmology & visual science 32: 1678-1692.

(56) References Cited

OTHER PUBLICATIONS

Tamm, S., E. Tamm, and J. W. Rohen. 1992. Age-related changes of the human ciliary muscle. A quantitative morphometric study. Mechanisms of ageing and development 62: 209-221.
Truscott, R. J. 2000. Age-related nuclear cataract: a lens transport problem. Ophthalmic research 32: 185-194.
Wang, C. J., Y. J. Hsieh, C. Y. Chu, Y. L. Lin, and T. H. Tseng. 2002. Inhibition of cell cycle progression in human leukemia HL-60 cells by esculetin. Cancer letters 183: 163-168.
Wang, S. J., and H. H. Chen. Jan. 2007. Presynaptic mechanisms underlying the alpha-lipoic acid facilitation of glutamate exocytosis in rat cerebral cortex nerve terminals. Neurochemistry international 50: 51-60.
Weeber, HA et al. Feb. 2007. Stiffness gradient in the crystalline lens. Graefes Arch Clin Exp Ophthalmol 245(9):1357-66.
Widomska, J., M. Raguz, J. Dillon, E. R. Gaillard, and W. K. Subczynski. Jun. 2007. Physical properties of the lipid bilayer membrane made of calf lens lipids: EPR spin labeling studies. Biochimica et biophysica acta 1768: 1454-1465.
Wieboldt, R. et al. 1994. Photolabile precursors of glutamate: Synthesis, photochemical properties, and activation of glutamate receptors on a microsecond time scale. Proc. Natl. Acad. Sci, 91:8752-8756.
Willner I & Zahavy E. 1994. Activation of Glutathione Reducase by Light: A Novel Approach to Design Redox Photo-Enzymes. Angew Chem Int Ed Engl 33(5):581-83.
Yin MC, et al. 2002. Nonenzymatic antioxidant activity of four organosulfur compounds derived from garlic. J Agric Food Chem. 50(21):6143-7.
Yu, N. T., D. C. DeNagel, P. L. Pruett, and J. F. Kuck, Jr. 1985. Disulfide bond formation in the eye lens. Proceedings of the National Academy of Sciences of the United States of America 82: 7965-7968.
Zhao, Y., Q. Zheng, K. Dakin, K. Xu, M. L. Martinez, and W. H. Li. 2004. New caged coumarin fluorophores with extraordinary uncaging cross sections suitable for biological imaging applications. Journal of the American Chemical Society 126: 4653-4663.
Zivkovic, D. Apr. 2007. Investigations on 2,7-diamino-9-fluorenol photochemistry. Inaugural Dissertation at Universität Basel.
Ip C, Ganther HE. 1992. Comparison of selenium and sulfur analogs in cancer prevention. Carcinogenesis. 13(7): 1167-70.
Bustamante, J., et al., 1998. α-Lipoic Acid in Liver Metabolism and Disease. Free Radical Biology & Medicine 24: No. 6 1023-1039.
Cagini, C. MD, et al. 2010. Study of alpha-lipoic acid penetration in the human aqueous humour after topical administration. Clinical and Experimental Ophthalmology "Accepted Article" doi: 10.1111/j.1442-9071.2010.02319.x.
Giblin FJ, et al. 1979. The effects of X-irradiation on lens reducing systems. Investigative Ophthalmology & Visual Science 18:468-475.
Kramár P, et al. 1987. Thermal cataract formation in rabbits. NCBI Pubmed abstract, PMID: 3426637, abstract of Bioelectromagnetics 8:397-406.
Li, X., Liu, Z., et al. Apr. 2008. Lipoamide protects retinal pigment epithelial cells from oxidative stress and mitochondrial dysfunction. Free Radic Biol Med. 44(7): 1465-1474.
Lipman RM, et al. 1988. Cataracts induced by Microwave and Ionizing Radiation. NCBI Pubmed abstract, PMID: 3068822, abstract of Surv. Ophthalmol 33:200-210.
Trayhurn P. and Van Heyningen R. 1973. The Metabolism of Amino Acids in the Bovine Lens; Their Oxidation as a Source of Energy. Biochem. J. 136:67-75.

Wakabayashi, Y. et al. 2006. Glutamate Levels in Aqueous Humor of Patients with Retinal Artery Occlusion. Retina 26:432-436.
Zwingmann, C. et al. 2001. 13C Isotopomer Analysis of Glucose and Alanine Metabolism Reveals Cytosolic Pyruvate Compartmentation as Part of Energy Metabolism in Astrocytes. GLIA 34:200-212.
Aloisi et al. 1948. Glycerylphosphorylcholine and Choline Glycerophosphate. Biochemical Journal. vol. 43, pp. 157-161; p. 157, col. 1, para 2-3; col. 2, para 1; p. 158, col. 1, para 4.
Gilbert, Basic Concepts in Biochemistry USA. McGraw Hill 2000 p. 184.
Jablonski et al. Plant Physiology 1978 61:221-225.
Ng et al. Experimental Eye Research 1986 43:477-489.
Morris Jr. Recent advances in arginine metabolism; roles and regulation of the arginases. British Journal of Pharmacology, E-Pub Jun. 5, 2009, 157(6):922-930.
PubChem Compound Summary CID 863 lipoamide (Sep. 16, 2004) (Retrieved from the internet Nov. 13, 2010; http://pubchem.ncbi.nlm.nih.gov/summary/summary.cgi?cid=863.
Salceda, et al. L-arginine uptake in normal and diabetic rat retina and retinal pigment epithelium. Neurochem Res., Aug. 2008, 33(8):1541-1545.
Stuehr et al. Nw-Hydroxy-L-arginine is an intermediate in the Biosynthesis of nitric Oxide from L-Arginine. The Journal of Biological Chemistry 1991, 266(10):6259-6263.
Truscott. Presbyopia. Emerging from a blur towards an understanding of the molecular basis for this most common eye condition. Exp Eye Res., Epub Jul. 2008, 88(2):241-247; p. 241, col. 1; p. 242, col. 1; p. 245, col. 1.
English Translation of Office Action mailed Jun. 21, 2011, in Japanese Patent Application No. JP 2007-537922 A, filed Dec. 27, 2007.
Extended European Search Report mailed on Apr. 19, 2012, for EP Application No. 09825411.0, European Patent Office, Germany.
Office Action received in U.S. Appl. No. 12/815,586 dated May 9, 2012.
Extended European Search Report mailed on Aug. 21, 2012, for EP Application No. 10790038,3, European Patent Office, Netherlands.
English Translation of Office Action mailed Oct. 12, 2012, in Mexican Patent Application No. MX/a/2007/004775.
Co-pending U.S. Appl. No. 14/170,116, inventors Garner et al., filed Jan. 31, 2014 (Not Published).
Co-pending U.S. Appl. No. 14/303,405, filed Jun. 12, 2014, inventors Garner et al., filed Jan. 31, 2014 (Not Published).
Glasser, A., "Restoration of accommodation: surgical options for correction of presbyopia," Clin Exp Optom 91(3):279-295, Australian Optometrists Association, Australia (May 2008).
McGinty, S. J., and Truscott, R. J. W., "Presbyopia: the first stage of nuclear cataract?" Opthalmic Res 38(3):137-148, Karger, Switzerland (Jan. 2006).
Michael, R., and Bron, A. J., "The ageing lens and cataract: a model of normal and pathological ageing," Phil. Trans. R. Soc. B 366(1568):1278-1292, The Royal Society, England (Mar. 2011).
Truscott, R J. W., and Zhu, X., "Presbyopia and cataract: a question of heat and time," Prog Retin Eye Res 29(6):487-499, Elesevier Ltd., England (Nov. 2010).
Petrash, J.M., "Aging and Age-Related Diseases of the Ocular Lens and Vitreous Body," Invest. Opthalmol. Vis. Sci. 54:ORSF54-ORSF59, The Association for Research in Vision and Opthamology. Inc., United States (Dec. 2013).

\* cited by examiner

PRESBYOPIA TREATMENT BY LENS ALTERATION

CROSS-REFERENCE TO RELATED APPLICATIONS

This application is a divisional of U.S. patent application Ser. No. 13/028,766 filed Feb. 16, 2011, now U.S. Pat. No. 8,747.829, which is a divisional of U.S. patent application Ser. No. 11/010,436 filed Dec. 14, 2004, now U.S. Pat. No. 7,935,332, which is a continuation of U.S. patent application Ser. No. 10/050,879 filed Jan. 18, 2002, now U.S. Pat. 6,923, 955, which claims benefit of the filing date of U.S. provisional application No. 60/264,423 filed Jan. 19, 2001 and is a continuation-in-part of U.S. patent application Ser. No. 09/930, 287 filed Aug. 16, 2001, now abandoned, which claims benefit of the filing date of U.S. Provisional Application No. 60/225,659 filed Aug. 16, 2000. The entire content of each of these applications is incorporated by reference herein.

FIELD OF THE INVENTION

The present invention relates to a method and device for reversing and treating presbyopia.

BACKGROUND OF THE INVENTION

Presbyopia affects virtually every person over the age of 44. According to Jobson Optical Database, 93% of people 45 and over are presbyopic. Presbyopia entails the progressive loss of amplitude of accommodation that occurs with aging. Adler's Physiology of the Eye, which is incorporated herein by reference, discloses that the human accommodative amplitude declines with age such that accommodation is substantially eliminated by the age of 50 to 55. Accommodative ability, as defined by U.S. Pat. No. 5,459,133 to Neufeld and incorporated in its entirety herein by reference for background information, is the capacity of the eye to focus for near vision by changing the shape of the lens to become more convex.

The ocular tissues involved in the accommodative response include the lens, the zonules, the lens capsule, and the ciliary muscle. Of these, the lens is the central tissue. These structures function together to enable the eye to focus on close objects by changing the shape of the lens. The lens is centrally suspended between the anterior and posterior chambers behind the pupillary opening of the iris. The lens is supported by an array of radially oriented zonular fibers, which extend from the lateral edges of the lens to the inner border of the circumferential ciliary muscle. The ciliary muscle is attached to the scleral coat of the eye. When the eye is at rest, it is focused for distance and the lens is in a somewhat flattened or less convex position. This shape is due to the tension that is exerted on the lens periphery by the zonules. The zonules pull the edges of the lens toward the ciliary body.

During accommodation, the shape of the lens becomes more convex through contraction of the ciliary muscle, which allows the ciliary attachment of the zonules to move toward the lens, reducing the tension in the anterior zonules. This reduction in tension allows the central region of the lens to increase in convexity, thereby enabling near objects to be imaged on the retina. The processes involving the coordinated effort of the lens, zonules, ciliary body, medial rectus muscles and iris, among others, that leads to the ability of the eyes to clearly focus near on the retina is the accommodative process.

Several theories have been advanced to explain the loss of accommodation with age. These theories include the hardening of the lens with age, loss of strength in the ciliary muscle, factors related to the physical growth of the lens, and, the loss of elasticity of the lens capsule. As for the loss of strength of the ciliary muscle, it is noted that although there are age-related morphological changes that occur, there is little evidence of diminishing strength of the ciliary muscle. In fact, under the influence of pilocarpine, the ciliary muscle will vigorously contract even in presbyopic eyes.

The lens grows throughout one's life and theories have been proposed that it is this increase in size that prohibits the effects of the zonules from affecting a change in the shape of the lens. Recent works exploring this possibility have not met widespread acceptance thus far. Most of the growth of the lens is not in its diameter, but instead, in its anterior-posterior dimensions.

As for changes in the lens capsule, it has been postulated that reduction in the elasticity of the capsule is, in fact, a contributing factor in presbyopia. Moreover, it has been found that Young's modulus of elasticity for the lens capsule decreases by nearly 50% from youth to age 60, while accommodation decreases by 98%. Consequently, the principal cause of presbyopia is now considered to be "lenticular sclerosis" or the hardening of the lens.

A cataract is a condition in which the lens becomes less clear. The study of cataracts lends insight into lens and capsular changes. The usual senile cataract is relatively discus-shaped when removed from the eye, its shape being dictated by the firm lens substance. The liquefied hypermature cataract is globular when extracted, rounded up by the elastic lens capsule. This is indirect evidence that it may be possible to reverse the lenticular changes associated with presbyopia, and that the lens capsule is still sufficiently elastic.

At the present time, common treatments for presbyopia include reading glasses, bifocal glasses, or mono-vision contact lenses. All of these solutions necessitate the use of an appliance creating additional shortcomings.

Alternative theories for treating presbyopia include scleral expansion and corneal reshaping. The efficacy of such techniques is not well-established and, importantly, these techniques do not attempt to reverse what the inventors of the subject-application believe to be a substantial causation, as explained more fully below, in the loss of the accommodative amplitude of the lens typically associated with the normal aging process. Moreover, because scleral expansion and corneal reshaping involve macroscopic changes in the morphology of the lens and/or cornea it fails to reverse presbyopia.

Finally, the use of the excimer laser for the purposes of corneal reshaping to produce a multifocal refracting surface has been disclosed in U.S. Pat. No. 5,395,356. While this method seems promising, it still requires structural changes to the cornea to compensate for aging changes in the lens. Rather than trying to undo the changes brought on by presbyopia, techniques such as these merely compensate for the loss of accommodative function by altering another ocular structure.

SUMMARY OF THE INVENTION

While not wishing to be bound to any particular theory, it is now believed that presbyopia is caused by the hardening of the lens, which can be due to an alteration of the structural proteins or an increased adhesion between the lens fibers. It is also believed that the intralenticular viscosity increases with age as a result of the formation of certain chemical bond structures within the lens. Accordingly, the present invention is directed to method and apparatus for preventing and or reversing presbyopia through treatment of the lens such that the viscosity of the lens is reduced, restoring the elasticity and movement to the lens fibers and increasing the accommodative amplitude of the lens.

The claimed invention is also directed to a method of reversing or treating presbyopia resulting in underlying changes in the structures and/or interactions of molecules comprising those components of the eye associated with the accommodative process, most notably the lens and/or lens capsule.

In an embodiment, the present invention provides a novel molecular approach to reversing presbyopia by restoring the accommodative amplitude of the lens, and in another preferred embodiment, to reversing presbyopia while also reducing the tendency for the lens to lose its thus restored accommodative amplitude.

In another embodiment of the invention the onset of presbyopia is prevented by regularly administered treatment where elasticity and the accommodative ability of the lens is restored. By applying the treatments as described herein to the eyes of persons in their mid to late 30's, or even younger, the on-set of presbyopia, as defined by a loss of accommodation, such that the accommodative power of the eye is below 2.5 Diopters, can be avoided. In one embodiment of the invention, such treatments whether for the purposes of preventing or reversing presbyopia, would be occasionally repeated during the course of a patient's lifetime. The frequency of the treatment would be determined by the degree of accommodative loss that needs to be recovered, the amount of accommodation that can be safely restored in a single procedure, and the amount of restoration desired.

In one embodiment, the present invention is directed to a method for reversing and/or treating presbyopia by breaking disulfide bonds in molecules comprising the structures of the eye, most notably the lens and the lens capsule, in which disulfide bonds are believed to be a substantial factor in the progressive loss of accommodative amplitude. In another embodiment, the breaking of the disulfide bonds is accompanied by chemical modification of the sulfur moiety in the cysteine molecule formed upon breaking of the disulfide bonds, such chemical modification rendering the sulfur moiety less likely to form new disulfide bonds. This method thus comprises a method for preventing, and/or reducing the recurrence of presbyopia by reducing the probability of forming new disulfide bonds. Particularly, this invention affects a change in the accommodative amplitude of the human lens by: (1) using various reducing agents that cause a change in the accommodative abilities of the human lens, and/or (2) the use of applied energy to affect a change in the accommodative abilities of the human lens. It is believed that by breaking bonds, such as disulfides, that crosslink lens fibers together and increase lens viscosity causing a hardening of the lens cortex and lens nucleus, the present invention increases the elasticity and the distensibility of the lens cortex, lens nucleus, and/or the lens capsule.

Presbyopia, or the loss of the accommodative amplitude of the lens, has often advanced in a typical person age 45 or older to the point where some type of corrective lens in the form of reading glasses or other treatment is required. It is to be understood that loss of accommodative amplitude can occur in persons much younger or older than the age of 45, thus the present invention is not to be construed as limited to the treatment of presbyopia in a person of any particular age. The present invention is most useful in a person whose accommodative amplitude has lessened to a point where restoration thereof to some degree is desirable. However the invention should not be limited to the correction of presbyopia, but may be used to prevent presbyopia from occurring.

In one embodiment of the present invention, the method of reversing or preventing presbyopia will result in an increase in the accommodative amplitude at least about by 0.5 diopters. In another embodiment of the present invention, the method of reversing or preventing presbyopia will result in an increase in the accommodative amplitude of at least about 2.0 diopters.

In still another embodiment, the method of reversing or preventing presbyopia of the present invention will result in an increase in the accommodative amplitude by at least about 5 diopters. In another embodiment of the present invention, the method of reversing or preventing presbyopia of the present invention will result in an increase of the accommodative amplitude of the lens to restoration thereof to that of a lens with a normal accommodative amplitude of 2.5 diopters or greater. It is noted that while it is obviously most beneficial to restore the accommodative amplitude of the lens to a normal accommodative amplitude, lesser degrees of restoration are also beneficial. For example, in some cases advanced presbyopia can cause severe reduction in the accommodative amplitude, thus making a complete restoration of the amplitude improbable.

DETAILED DESCRIPTION

The accommodative amplitude of the lens is measured in diopters (D). The loss of accommodative ability begins at a very early age, such that by age 10 the average eye has 10 D, age 30, 5 D, and by age 40, only 2.5 D of accommodative power. The lens of a person who does not suffer from presbyopia (i.e. a person whose lens accommodates normally), will typically have an accommodative amplitude of about 2.5 diopters or greater. The terms "reversing presbyopia" or "treating presbyopia" as used herein mean increasing the accommodative amplitude of the lens.

As stated, inelasticity of the lens, or hardening thereof, is believed to be a contributing cause of presbyopia. The hardening of the lens can be due to an alteration of the structural proteins or an increased adhesion between the lens fibers. Additionally, it is believed that the lens viscosity also increases with age due to an increased concentration of certain chemical bond structures within the lens. In one embodiment, the present invention is directed to treating presbyopia by altering the molecular and/or cellular bonds between the cortical lens fibers so as to free their movement with respect to each other. The increased elasticity of the lens apparatus can restore lost amplitude of accommodation. Specifically, it is believed that disulfide bonds in the molecules comprising the structures of the eye responsible for proper accommodation are a substantial factor in the hardening of the lens and the concomitant loss of accommodative amplitude.

Thus, in one embodiment of the invention treatment process involves breaking the disulfide bond and then protonating the newly formed sulfur moiety with a reducing agent such as glutathione to impart a hydrogen atom thereto. The steps can be performed simultaneously or consecutively. In either case, the reducing agent can be present at the time the disulfide bond is broken in order to eliminate reformation of disulfide. That is, the reducing agent can introduce and bond a moiety onto the free sulfur after breaking the disulfide bond such that the likelihood of reformation of another disulfide bond is prevented or at least reduced. While the reducing agent may introduce a hydrogen atom onto the free sulfur, thus forming a sulfhydryl group (—SH), the resultant —SH groups can again be oxidized to form a new disulfide bond. Thus, it is advantageous to introduce a group into the free sulfur moiety, such as lower alkyls, methylating compounds, or other agents, which reduce the tendency of new disulfide bond formation. This method can result in a substantial prevention of the reoccurrence of presbyopia.

As stated, it is believed that the disulfide bonds form both between the lens fibers, between lens proteins, and between lens proteins and various thiols both within and on lens fibers. These bonds and substantially reduce the lens fibers' ability to easily move relative to each other and thus the ability of the lens to accommodate properly. While not wishing to be bound by any particular theory, the bonds may form by way of absorption of light energy, which causes the sulfhydryl bonds on the lens proteins to oxygenate removing a hydrogen atom from two adjacent —SH groups and creating water and a disulfide bond. Reducing the disulfide bonds requires hydrogen donors such as glutathione or other molecules. Other possible theories involve protein-thiol mixed disulfide bonds forming such as protein-S—S-glutathione or protein-S—S-cysteine. Glutathione therefore may be both part of the solution and part of the problem. The use of Glutathione in any treatment regimen therefore must be monitored carefully in light of the potential for an increase in undesirable bond formation.

The total refractive power of the lens is greater than what would be expected based on the curvature and the index of refraction. As stated, contraction of the ciliary muscle causes the ciliary body to move forward and towards the equator of the lens. This causes the zonules to relax their tension on the lens capsule, which allows the central lens to assume a more spherical shape. During accommodation, the main change is in the more central radius of curvature of the anterior lens surface, which is 12 mm in the unaccommodative state and can be 3 mm centrally during accommodation. Both the peripheral anterior and the posterior lens surfaces change very little in curvature during accommodation. The axial thickness increases while the diameter decreases. The central anterior lens capsule is thinner than the rest of the anterior capsule. This may explain why the lens bulges more centrally during accommodation.

The thinnest portion of the capsule is the posterior capsule, which has a curvature greater than the anterior capsule in the unaccommodative state. The protein content of the lens, almost 33% by weight, is higher than any other organ in the body. There are many chemical compounds of special interest in the lens. For example, glutathione is found in high concentration in the lens cortex even though there is very little in the aqueous. Thus, the lens has a great affinity for glutathione and actively absorbs, transports and synthesizes glutathione. Approximately 93% of intralenticular glutathione is in the reduced form. Glutathione may be involved with maintaining the lens proteins, the sulfhydryl groups (—SH), in their reduced states. That is, after the disulfide bond is broken and the sulfur moieties are made available, glutathione can impart a hydrogen atom to form the sulfhydryl group thereby preventing or minimizing the reformation of a disulfide bond. In addition, ascorbic acid can also be found in very high concentrations in the lens. It is actively transported out of the aqueous and is at concentrations 15 times that found in the bloodstream. Both inositol and taurine are found at high concentrations in the lens for which the reason is not known.

According to one embodiment of the invention, the increase in the accommodative amplitude is accomplished by treatment of the outer lens region (the cortex) or the inner layer (the nucleus) with radiation, sonic or electromagnetic energy, heat, chemical, particle beam, plasma beam, enzyme, gene therapy, nutrients, other applied energy source, and/or any combination of any of the above sufficient to break the disulfide bonds believed responsible for the inelasticity of the lens. Chemicals are useful to reduce disulfide bonds that are believed to anchor lens fibers hence preventing their free movement and elasticity. By making the anterior cortex and/or the nucleus more elastic, viscosity is lowered and the lens is again able to assume its characteristic central bulge during accommodation.

Chemicals suitable for Causing reduction include, by way of example only, glutathione, ascorbic acid, Vitamin E, tetra-ethylthiuram disulfyl, i.e., reducing agent, any biologically suitable easily oxidized compound, ophthalmic acid, inositol, beta-carbolines, any biologically suitable reducing compound, reducing thiol derivatives with the structure:

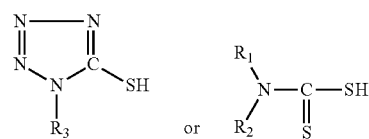

or sulfur derivatives with the structures:

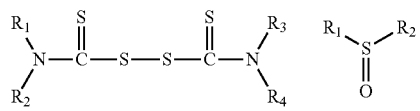

Wherein $R_1$, $R_2$, $R_3$ and $R_4$ are independently a straight or branched lower alkyl that may be substituted, e.g., by hydroxyl, lower alkoxy or lower alkyl carbonyloxy, their derivatives or a pharmaceutically acceptable salt thereof. Preferred exemplary reducing agents include diethyl dithiocarbamate, 1-methyl-1H-tetrazol-5-yl-thiol and 1-(2-hydroxyethyl)-1H-tetrazol-5-yl-thiol or and pharmaceutically acceptable salts thereof. Other useful compounds can be found in U.S. Pat. No. 5,874,455, which is hereby incorporated in its entirety by reference for background information. The above-mentioned chemicals are merely exemplary and other reducing agents that behave similarly by breaking the disulfide bond are included within the scope of this invention.

The chemical reducing agents can be used alone or in conjunction with a catalyst such as an enzyme. Enzymes and other nutrients suitable for causing or facilitating reduction include, for example, aldoreductase, glyoxylase, glutathione S-transferase, hexokinase, thiol reductase, thioltransferase, tyrosine reductase or any compatible reductase. The need for a source of applied energy for the reduction of the disulfide bonds may be met by the addition of glucose-6-phosphate, which is present within the lens but the enzyme, hexokinase that normally converts the glucose to the G6P energy state is rendered non-functional by the process of thiol oxidation. Again, it should be noted that the above-listed enzymes are exemplary and not an exhaustive list. The enzymes can be naturally present in the eye, or can be added to the eye together with or separate from the chemical reducing agent or energetic means disclosed herein. As such, other chemically and biologically comparable enzymes that help break disulfide bonds or behave similarly should be considered as within the scope of the present invention.

In one embodiment of the invention, the reduction of disulfide groups of the lens proteins to sulfhydryl groups is accomplished by delivering to the lens a compound such as glutathione, thiols, or others in sufficient quantities to reduce the disulfide bonds and other molecular and cellular adhesions. Other enzymes or chemicals that affect a methylation on the free sulfur atom include for example, methyl-methane thiosulfonate, methyl glutathione, S-methyl glutathione, S-transferase and other biologically compatible methylating agent. Use of emulsions such as nanocapsules, albumin microspheres, carrier molecules such as inositol, taurine or other biologically suitable means such as virus phages for delivering the reducing agent or enzymes to the dens is an integral part of this invention. The chemical reducing agent will typically be delivered in the form of a solution or suspension in an ophthalmically acceptable carrier. In some cases, the application of energy to affect or catalyze the reduction of the disulfide bonds as well as the disruption of other bonds and adhesions may be beneficial. The application of energy alone can be used to break the disulfide bonds. Applied energy can have any form, by way of example only, any of laser, ultrasound, particle beam, plasma beam, X-ray, ultraviolet, visible light, infrared, heat, ionizing, light, magnetic, microwave, sound, electrical, or other not specifically mentioned, can be used alone or in combination with the reducing agents to affect the treatment of presbyopia, or a combination of any of these types of energies.

In a similar manner, agents can be delivered to the lens capsule, which bind or interact with the capsule to affect greater elasticity or distensibility. Such agents either cause the capsule to shrink in surface area or increase the tension of the lens capsule on the peripheral anterior or posterior of the lens. Applied energy can have any form, by way of example only, any of laser, ultrasound, heat, particle beam, plasma beam, X-ray, ultraviolet, visible light, infrared, ionizing, light, magnetic, microwave, sound, electrical, or other not specifically mentioned can be used alone or in combination with the reducing agents to affect the treatment of presbyopia or a combination of any of these types of applied energy.

In another embodiment of the invention, applied energy can be used as a catalyst to induce or increase the rate of the reduction reaction. Thus, by applying energy, the peripheral portion of the capsule is preferentially affected, leaving the central 4 mm zone of accommodation unaffected. This allows the lens to assume a more accommodative state. The applied energy can also be applied alone to promote the reduction reaction and the cellular changes that ultimately affect the lens cortex. As examples, lasers useful in the present invention include: excimer, argon ion, krypton ion, carbon dioxide, helium-neon, helium-cadmium, xenon, nitrous oxide, iodine, holmium, yttrium lithium, dye, chemical, neodymium, erbium, ruby, titanium-sapphire, diode, femtosecond or attosecond laser, any harmonically oscillating laser, or any other electromagnetic radiation. Exemplary forms of heating radiation include: infrared, heating, infrared laser, radiotherapy, or any other methods of heating the lens.

Finally, exemplary forms of sound energy that can be used in an embodiment of the invention include: ultrasound, any audible and non-audible sound treatment, and any other biologically compatible sound energy.

In still another embodiment of the present invention, radiation, such as ultraviolet light, visible light, infrared, microwave, or other electromagnetic energy may be placed in the eye to help break the disulfide bonds. This would then make it possible for the reduction of the disulfide bonds to occur.

The applied energy used with various embodiments and methods of the present invention could be applied through either contact with the sclera or cornea, non-contact techniques, or through intraocular methods of delivery. More than one treatment may be needed to affect a suitable increase in the accommodative amplitude. When more than one modality of treatment is desirable, chemical treatment can be administered prior to, after, or simultaneously with the application of energy.

What is claimed is:

1. A method for reversing the effects of presbyopia comprising:
    applying an external energy source to a lens of an eye; and
    administering a reducing agent to the lens to reduce the likelihood of reformation of lenticular disulfide bonds.

2. The method of claim 1 where the energy is of sufficient power to break lenticular disulfide bonds.

3. The method of claim 1, wherein the energy is any form of electromagnetic radiation.

4. The method of claim 1, wherein the energy is any form of sound energy.

5. The method of claim 1, wherein the energy is any form of heat.

6. The method of claim 1, wherein the reducing agent is glutathione, ascorbic acid, a thiol derivative, vitamin E, tetraethylthiuram disulfyl, ophthalmic acid, inositol, or a beta-carbolise.

7. The method of claim 1, further comprising administering to the lens a methylating agent selected from the group consisting of methyl-methane thiosulfonate, methyl glutathione, S-methyl glutathione, S-transferase, and other biologically compatible methylating agents, wherein the reducing agent is capable of reducing the disulfide bonds into sulfhydryl groups; and wherein the methylating agent is capable of methylating the sulfhydryl groups.

8. The method of claim 7, wherein the methylating agent comprises methyl-methane thiosulfonate.

9. The method of claim 7, wherein the methylating agent comprises methyl glutathione.

10. The method of claim 7, wherein the methylating agent comprises S-methyl glutathione.

11. The method of claim 7, wherein the methylating agent comprises S-transferase.

12. The method of claim 1, wherein the lens is a lens of a human eye.

13. The method of claim 1, further comprising administering a catalyst to the lens.

14. The method of claim 13, wherein the catalyst is selected from the group consisting of a reductase, an aldoreductase, a glyoxylase, a glutathione S-transferase, a thiol reductase, a tyrosine reductase, and a hexokinase.

* * * * *